United States Patent [19]

Pearlman

[11] Patent Number: 4,853,388
[45] Date of Patent: Aug. 1, 1989

[54] METHOD FOR TREATING PSORIASIS WITH CYTOTOXIC AGENTS

[76] Inventor: Dale L. Pearlman, 21063 Christensen Dr., Cupertino, Calif. 95014

[21] Appl. No.: 50,983

[22] Filed: May 15, 1987

[51] Int. Cl.$^4$ ............................................. A61K 31/505
[52] U.S. Cl. ...................................... 514/274; 514/863
[58] Field of Search ................................ 514/274, 563

[56] References Cited

U.S. PATENT DOCUMENTS 3,989,816 11/1976 Rajadhyaksha ........................ 424/60
4,423,040 12/1983 Rajadhyaksha ...................... 424/180
4,636,509  1/1987 Phillipps et al. ...................... 514/274
4,705,791 11/1987 Bemeche et al. ..................... 514/274

OTHER PUBLICATIONS

Pearlman et al., J. Am. Acad. Dormatol. vol. 17, No. 1, pp 78–82 (1987).
Pearlman et al. J. Am. Acad. Dermotol. 15:1247–52, 1986.
Peck et al., "Topical Lomustine in the Treatment of Psoriasis." Arch. Derm. 106:172–176 (1972).

*Primary Examiner*—Leonard Schenkman
*Attorney, Agent, or Firm*—William B. Walker

[57] ABSTRACT

A method for treating psoriasis comprising applying an effective amount of a cytotoxic drug dispersed in a pharmaceutically acceptable vehicle containing a penetrating solvent for the drug, the drug being applied to the skin area affected by the psoriasis without occlusion in pulses of from 1 to 3 applications per pulse, the pulses being applied at an interval of once every from 3 to 30 days and preferably at an interval of from 4 to 14 days. Optimally, the penetrating solvent is free from toxic effects, such as AZONE or similar substituted azacycloalkyl-2-ones, tertiary amine oxides, and the like.

10 Claims, No Drawings

METHOD FOR TREATING PSORIASIS WITH CYTOTOXIC AGENTS

FIELD OF THE INVENTION

This invention relates to the therapeutic treatment of skin disorders such as psoriasis. In particular, this invention relates to an effective regimen for successfully treating psoriasis with a cytotoxic agent such as 5-fluorouracil in a penetrating solvent.

BACKGROUND OF THE INVENTION

Psoriasis is a chronic, hereditary, recurrent, papulosquamous dermatosis, the distinctive lesion of which is a vivid red macule, papule, or plaque covered almost to its edge by silvery lamellated scales. It usually involves the scalp and extensor surfaces of the limbs, especially the elbows, knees and shins.

Traditional treatments of psoriasis have included daily or more frequent application of corticosteroids such as betamethasone acetate, betamethasone valerate, fluocinolone acetonide, fluocinolone acetonide acetate, and the like dissolved or suspended in an ointment, lotion, or glycol solvent to the affected area. Occlusive techniques such as wrapping cortiocoid treated areas with a moisture-impermeable wrapping such as a self-attracting plastic film such as polyvinylidene chloride film (SARAN) has been found to increase the effectiveness of the treatment. Penetrating solvents have been investigated for enhancing percutaneous absorption of these drugs in an effort to more successfully treat more resistive conditions.

DESCRIPTION OF THE PRIOR ART

Fluorouracil (5-fluorouracil or 5-FU) is described as useful for the treatment of actinic keratosis, applied topically as a 1% cream or solution, once or twice daily, to the affected area in REMINGTON'S PHARMACEUTICAL SCIENCES. Mack Publishing: Easton, 15th ed. p 1079 (1975).

AZONE (1-dodecylazacycloheptan-2-one) is reported to enhance the percutaneous absorption of a variety of drugs including steroids and fluorouracil by Stoughton, R., *Arch.Dermatol.* 118:474–477 (1982). Prior use of dimethyl sulfoxide (DMSO), dimethylacetamide (DMA), dimethyl formamide (DMF), 1-methyl-2-pyrrolidone, and propylene glycol to enhance skin penetration of drugs was also disclosed.

Comparison of AZONE with other penetrating solvents such as propylene glycol and n-decylmethyl sulfoxide for enhancing penetration of fluorouracil is described by Touitou, E., *International Journal of Pharmaceutics.* 27:89–98 (1985). The writer characterizes 5-FU as a cytotoxic agent used topically on the skin in actinic kerotosis and various epithelial neoplasma, and states the need for improved therapy brought into use methods for increasing skin penetration such as use of occlusivity and chemical enhancing agents, citing Chen, Y., NOVEL DRUG DELIVERY SYSTEMS. Marcel Dekker: New York, p 192 (1982). Propylene glycol solutions are said to be the most popular, and the writer's presentation demonstrated that AZONE was a more effective penetrating agent than propylene glycol or n-decylmethyl sulfoxide in dilute concentrations. Sogibayashi, K. et al, *J. Pharm.Pharmacol.* 37:578–580 (1985) and Mourmoto, Y. et al, *International Journal of Pharmacology.* 32:31–38(1986) also describe enhanced absorption with AZONE across hairless rat skin, using 5-fluorouracil as a model drug.

U.S. Pat. No. 3,989,816 describes n-alkylazacycloheptan-2-ones wherein the alkyl group has from 1 to 18 carbons, and the use of these and related compounds to enhance percutaneous absorption or penetration of drugs. Among the extensive lists of drugs are antineoplastic agents such as fluorouracil. Treatment of psoriasis with steroids in the penetrating solvent is also disclosed. U.S. Pat. Nos. 3,989,815 and 3,991,203 describe use of bis-azacyclopentan-only alkanes and 1-substituted azacyclopentan-2-ones, respectively, as penetrating agent. In a disclosure almost identical to U.S. Pat. No. 3,989,816, the inventor describes the treatment of psoriasis with steroids in the respective solvents, and lists fluorouracil as a suitable antineoplastic agent for use with the solvents.

U.S. Pat. No. 2,802,005 claims fluorouracil and describes it use as a germicidal agent or antimetabolite.

U.S. Pat. No. 4,565,806 describes treatment of skin cancer with cytostatic agents such as fluorouracil, colchicine, vinblastin sulfate, phloridzin, triethylene thiophosphamide, humic acid, and nitrogen mustards such as cyclophosphamide and mechlorethamine in DMSO. Percutaneous or intravenous administration are described. Suitable dosage levels and frequency recommended are said to be known to those skilled in the art.

U.S. Pat. No. 4,411,893 describes a novel water-soluble tertiary amine oxide useful to enhance of penetration of drugs through the skin. U.S. Pat. No. 3,326,768 is cited in the patent to show the use of a phosphine oxide surfactant in a topical preparation. U.S. Pat. No. 3,472,931 is also referenced, disclosing the use of a vehicle containing a lower alkyl amide to enhance percutaneous absorption. Use of the absorption enhancers with hydrocortisone to treat inflammation and with 5-fluorouracil for the treatment of actinic keratosis is also disclosed.

U.S. Pat. No. 3,996,924 describes the treatment of psoriasis with a combination of corticosteroid and 5-fluorouracil in a suitable topical ointment or solution carrier. Included in an omnibus listing of possible carrier ingredients are propylene glycols, dimethyl sulfoxide and dimethyl formamide. Daily application, preferably with a continuous occlusive dressing is recommended.

The prior art describes the application of cytotoxic agents in penetrating solvents applied once or more daily. Concurrent use with an occlusive dressing is indicated. In fact, the extreme inflammatory reaction caused by the cytotoxic damage to treated skin seen in continuous daily dosing schedules has heretofore prevented the practical use of these solvent systems to enhance percutaneous absorption of cytotoxic agents.

The use of 5% fluorouracil solutions topically with traditional vehicles under continuous occlusion for 2 weeks have been reported by Tsuiji, T. et al. *Arch.Dermatol.* 105:208–212 (1972) as effective therapy for psoriasis, producing long remissions without systemic toxicity. However, the therapy produced such severe burns that hospitalization of the patient was required. When fluorouracil was applied every other day (3 times a week) with occlusion, erosions also occurred, limiting therapy, and remission was brief. Ljunggren, B. et al, *Arch.Dermatol.* 106:263 (1972). When fluorouracil was used without occlusion, and with a topical steroid continuously for 2 weeks, the degree of local toxicity was acceptable, but the degree of improvement and the duration of remission was not sufficient. Fredriksson, T., "Topical treatment of psoriasis with 5-fluorouracil and fluocinolone acetonide:," in Faber E. et al, editors: PSORIASIS: PROCEEDINGS OF THE THIRD INTERNATIONAL SYMPOSIUM, STANFORD UNIVERSITY, July 13–17 (1981). How to retain effectiveness while controlling local toxicity remained a challenging question.

SUMMARY OF THE INVENTION

This invention is a method for treating psoriasis comprising applying to the psoriatic lesion, an effective amount of a cytotoxic drug dispersed in a pharmaceutically acceptable vehicle containing a penetrating solvent for the drug. The drug is applied in a pulse of from 1 to 3 applications within a period of 48 hours to the skin area affected by the psoriasis without occlusion, and no further application is made for a period of from 3 to 30 days. This procedure is repeated until complete remission is effected.

Optimally, the penetrating solvent is free from toxic effects, such as AZONE or similar substituted azacycloalkyl-2-ones, tertiary amine oxides, and the like.

DETAILED DESCRIPTION OF THE INVENTION

I discovered that treatment of psoriasis using a weekly pulse dosing with topical applications of 5-fluorouracil with traditional vehicles under occlusion provided great improvement of the condition. Many patients had sustained remissions. Each week the patients had an average topical application pulse lasting 48 hours. I discovered that this weekly pulse dosing schedule eliminated the severe local toxicity seen with prior continuous daily dosing schedules. Dale Pearlman et al, J.Am.Acad.Dermatol. 15:1247–1252 (December, 1986).

While this therapy was quite effective, it took an average 15.7 weeks to achieve remission. I then discovered that the factor delaying remission was suboptimal tissue concentrations of 5-FU. By injecting 5-FU directly into the psoriatic tissue, I was able to achieve remission in an average of 4 weeks. Thus traditional vehicles, even under occlusion, are incapable of providing optimal transepidermal drug delivery.

This invention is based on the discovery that with effective delivery of a cytotoxic agent through the stratum corneum, a superior therapeutic response is obtained if an effective amount drug is administered in one 48 hour pulse followed by a sustained pause of from 3 to 30 days and preferably from 4 to 14 days. During the 48 hour pulse period, the drug can be applied to the psoriatic lesion a sufficient number of times to achieve the desired tissue concentration, usually from 1 to 3 times being sufficient. Most optimally, a single application of drug is made to the lesion once a week. Effective remission is obtained, usually within 45 days, without significant inflammation or other evidence of severe damage to treated tissue.

An effective method for achieving this result is the topical application of an effective concentration of the cytotoxic agent together with a penetrating solvent such as AZONE, water-soluble tertiary amine oxide, DMSO or the like as a "pulse application" at an interval of from 3 to 30 and preferably at an interval of from 4 to 14 days. During the 48 hour pulse period, the drug-penetrating solvent preparation is applied for a sufficient number of times to achieve the desired drug concentration in the tissue. With most psoriatic lesions, the desired drug concentration can be achieved by from 1 to 3 applications of the drug-penetrating solvent composition.

In the method of this invention, a cytotoxic drug, in a vehicle containing a penetrating solvent, is applied topically to a skin area affected by psoriasis.

Suitable cytotoxic agents include 5-fluorouracil, colchicine, vinblastine sulfate, cyclophosphamide, azathioprine, cyclocytidine, azacytidine, azaserine, cisplatin, cycloheximide, mechlorethamine, cycloleucine, cytarabine, decarbazine, dactinomycin, dichloromethotrexate, emetrine hydrochloride, etoposide, quanazole, hydroxyurea, idoxuridine, mercaptopurine, methotrexate, methyl GAG (methylglyoxal bis(guanylhydrazone)), metoprine, pyrimethamine, scopolamine hydrobromide, thioquanine, thiotepa, vincristine sulface, and cyclosporin A, 5-fluorouracil being preferred.

Suitable penetrating solvents are solvents for the cytotoxic agent which will enhance percutaneous penetration of the drug. Solvents which have this property include dimethyl sulfoxide, dimethylacetamide, dimethyl formamide, and 1-methyl-2-pyrrolidone, and to a far lesser extent, propylene glycol. Preferred and superior solvents for this purpose are essentially free from adverse side effects and include substituted azacycloalkan-2-ones having from 5 to 7 carbons in the cycloalkyl group such as 1-dodecylazacycloheptan-2-one (AZONE) and other azacycloalkan-2-ones described in U.S. Pat. No. 3,989,816 (hereby incorporated by reference in its entirety) and represented by Formula I:

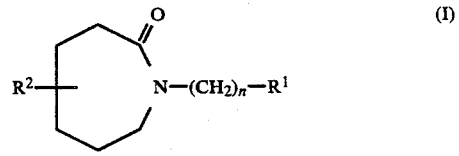

wherein
R$^1$ is a straight or branch chain alkyl group having from 1 to 18 carbons or aryl group having from 6 to 10 carbons;
R$^2$ is H or lower alkyl having from 1 to 4 carbons; and
n is an integer from 0 to 10.

Also included are N-bis-azacyclopentan-2-onyl alkanes described in U.S. Pat. No. 3,989,815 (hereby incorporated by reference in its entirety) and represented by Formula II:

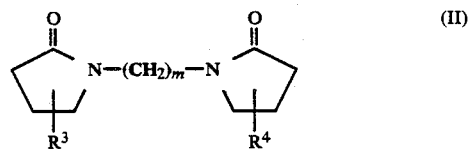

wherein
R$^3$ and R$^4$ are each H or a lower alkyl group having from 1 to 4 carbons; and
m is a positive integer of from 1 to 18.

Also included are 1-substituted azacyclopentan-2-ones described in U.S. Pat. No. 3,991,203 (hereby incorporated by reference in its entirety) and represented by Formula III:

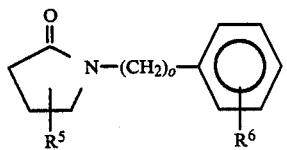

(III)

wherein $R_5$ and $R^6$ are each H or lower alkyl having from 1 to 4 carbons; and o is a positive integer from 0 to 10.

Also included are water-soluble tertiary amine oxides describe in U.S. Pat. No. 4,411,893 (hereby incorporated by reference in its entirety) and represented by Formulas IV and V:

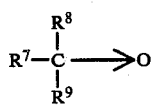

(IV)

wherein $R^7$, $R^8$ and $R^9$ are each saturated or unsaturated aliphatic radicals optionally containing ether or amide linkages and pendent hydroxyl groups, and the total number of carbon atoms of $R^7$, $R^8$ and $R^9$ does not exceed 28.

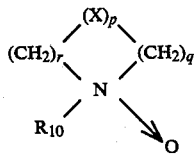

(V)

wherein

X is —O— or —N($R^{11}$)—;

$R^{10}$ and $R^{11}$ are each saturated or unsaturated aliphatic radicals having from 1 to 18 carbons and optionally containing ether or amide linkages and pendent hydroxyl groups; and p is 0 or 1;

q is 2, 3 or 4; and r is 2 or 3.

The topical formulation can be in the form of a lotion, cream, ointment, gel or solution, preferably a lotion, cream or solution containing a therapeutically effective amount of the cytotoxic drug and a sufficient proportion of penetrating solvent to solubilize the drug. Suitable drug concentrations will depend upon the choice of drug. Fluorouracil concentrations are from 0.001 to 5 weight percent and preferably from 1 to 5 weight percent.

For formulations with penetrating solvents of Formulas I, II and III, solutions or gels containing from 0.001 to 5 weight percent and preferably from 1 to 5 weight percent fluorouracil are preferred.

For formulations with penetrating agents such as the tertiary amine oxides of Formulas IV and V, the amine oxide and drug is incorporated into traditional lotions, gels and creams containing from 0.1 to 70 weight percent amine oxide, other traditional excipients, and water are preferred. These compositions can contain from 1 to 99 weight percent water.

A typical gel may contain, for example, one percent hydroxyethyl cellulose.

Typical lotion and cream formulations follows:

| LOTION | |
|---|---|
| Parts by Weight | Ingredient |
| 5 | polyoxylene-40-stearate |
| 3 | sorbitan monostearate |
| 12 | *mixture of lanolin, mineral oil and lanolin alcohol |
| 6 | cetyl alcohol |
| 20 | soybean oil |
| 53.7 | water |
| 0.2 | methyl paraben |
| 0.1 | propyl paraben |

*AMERCOL BL (Amerchol Corp, Edison, N.J.)

| CREAM | |
|---|---|
| Parts by Weight | Ingredient |
| 3 | polyoxyethylene-4-stearate |
| 2.5 | sorbitan monostearate |
| 10 | soybean oil |
| 10 | *mixture of lanolin, mineral oil and lanolin alcohol |
| 1 | cetyl alcohol |
| 73.2 | water |
| 0.2 | methyl paraben |
| 0.1 | propyl paraben |

*AMERCOL BL (Amerchol Corp, Edison, N.J.)

The composition containing the cytotoxic agent and penetrating solvent are applied to the skin are having the psoriasis in a quantity sufficient to wet or to cover to surface.

A critical aspect of this invention is the interval between pulses. In contrast to the previous methods of applying these agents, in penetrating solvents, they are applied according to this invention in single pulses at intervals of from 3 to 30 days and preferably at intervals of from 4 to 14 days. The procedure is repeated until the condition disappears. A total of from 1 to 6 application pulses is usually sufficient with fluorouracil.

When applied in accordance with this invention, the psoriasis disappears without extensive inflammation (erythma) of the treated skin surface. For patients with particular sensitivity to the cytotoxic agent, applications at longer intervals within the suggested range is suggested. If erythema begins to appear, the intervals should be lengthened until all signs of significant skin irritation disappear.

Occlusion is usually not necessary with the method of this invention. In a situation where the use of occlusion is believed necessary, the intervals between application times should be lengthened since cytotoxic agent damage to treated cells is usually increased by occlusive dressings.

Because the patient response will vary from patient to patient, the following examples include procedures for optimizing the parameters of drug concentration, number of applications per pulse, and the intervals between pulses. The preparations are applied initially once a week to the psoriatic lesions in an amount sufficient to moisten the surface. Depending upon the patient's response to the therapy, the physician can elect to continue the therapy in the same manner if progress is satisfactory or elect to vary any of the parameters. The concentration of drug and penetration agent can be varied until the desired amount of drug concentration in the tissue is obtained. Initially, one application per pulse can be used, and the period of exposure of the lesions to the drug is selected to achieve the desired amount of drug concentration in the tissue. The number of applications per pulse and the duration of the interval between pulses is determined by the response of the psoriasis to treatment and the time required for the treated skin to recover from exposure to the drug, timed to minimize local toxicity.

Once remission is achieved, physicians may choose two courses of treatment during remission. Preferably, no therapy is applied until relapse occurs. Then an appropriate therapy schedule is reinstated. Alternatively, in order to maintain a remission, maintenance therapy may be selected, applying drug/penetrating agent compositions delivering the lowest effective dose of drug with the longest intervals between applications still providing effective remission.

This invention is further illustrated by the following specific but non-limiting examples. In the examples, temperatures are given in degrees Centigrade and concentrations are given as weight percents, unless otherwise indicated. Examples constructively reduced to practice in filing this application are presented in the present tense, and examples describing procedures carried out in the laboratory or clinic are set forth in the past tense.

EXAMPLE 1

Titration of Drug Treatment Parameters

Solution A is prepared comprising 1 wt. % 5-FU, 2 wt. % AZONE, 50 wt % propylene glycol and the remainder, sterile, deionized water.

Solution A is applied to psoriasis of the knee once weekly in an amount sufficient to moisten the surface. If, at the end of two weeks, the response to the treatment is less than desired, a more concentrated solution (Solution B) is prepared containing 5 wt. % 5-FU, 2 wt. % AZONE, 50 wt. % propylene glycol and the remainder sterile, deionized water.

If the progress is still unsatisfactory, the application regiment is modified. Two applications of Solution B are applied in a pulse of two applications 12 hours apart. The interval between pulses is left unchanged. If the rate of progress is satisfactory, and no local toxicity is observed, the regimen is repeated with this concentration until complete remission is achieved.

EXAMPLE 2

Optimizing Pulse Timing Cream Composition

Cream A is prepared containing 5 wt. % 5-FU, 40 wt. % 1-benzylazacyclopentan-2-one and the remainder inert excipients which provide a stable cream composition (AMERCOL BL, described above).

Cream A is applied once weekly to psoriasis on the elbows in an amount sufficient to moisten the surface. If after 2 weeks the rate of progress is satisfactory but there is evidence of mild, local toxicity, a rest period of no therapy is instituted for one week to allow recovery from the toxicity. Treatment is then reinstated changing the interval between pulses to 2 weeks, leaving the formula and number of applications unchanged. If after 2 weeks, the rate of recovery is satisfactory, and no local toxicity is observed, the program is continued until remission is achieved.

EXAMPLE 3

Optimizing Lotion Composition

Lotion A is prepared with the following composition: 5-FU, 1 wt. %; N-bis-1,6(azacyclopentan-2-onyl)hexane, 20 wt %.; cetyl alcohol, 15 wt. %; propylene glycol, 10 wt. %; sodium lauryl sulfate, 15 wt. %; and sterile, deionized water qs. ad.

The patient begins treatment with the lotion applied once a week in an amount sufficient to moisten the surface of the psoriatic lesion. If after 2 weeks, the rate response is inadequate though no local toxicity is observed, Lotion B is prepared having the following ingredients: 5-FU, 5 wt. %; N-bis-1,6(azacyclopentan-2-onyl)hexane, 20 wt %.; cetyl alcohol, 15 wt. %; propylene glycol, 10 wt. %; sodium lauryl sulfate, 15 wt. %; and sterile, deionized water qs. ad. Lotion B is applied once a week in an amount sufficient to moisten the surface.

If after 2 weeks, the rate of response is still inadequate without local toxicity, the number of applications per pulse is increased to 3 separate applications with a separation of 12 hrs between applications, with no change in formula or interval between pulse doses. If after 2 weeks, the rate of progress is improved, but slight local toxicity is observed, the interval between pulses is increased to 2 weeks with the other parameters remaining unchanged.

If after two weeks, the rate of progress is adequate and no local toxicity is observed, the therapy regimen in repeated without change until complete remission occurs.

I claim:

1. A method for treating psoriasis consisting essentially of applying a therapeutically sufficient quantity of a composition consisting essentially of 5-fluorouracil dissolved in a penetration enhancing agent to a psoriatic lesion until remission occurs, the composition being applied in one or more pulses at about one week intervals, each pulse comprising applying to the lesion one or more times over a period of up to 48 hours, an amount of the composition sufficient to wet the lesion.

2. The method of claim 1 wherein the penetration enhancing agent includes propylene glycol.

3. The method of claim 2 wherein a solution of from 0.001 to 5 wt. % 5-fluororacil in propylene glycol is applied to psoriatic lesion.

4. The method of claim 1 wherein the penetration enhancing agent includes compound of Formula I, II or III:

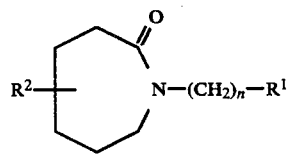

wherein
R$^1$ is a straight or branch chain alkyl group having from 1 to 18 carbons or aryl group having from 6 to 10 carbons;
R$^2$ is hydrogen or lower alkyl having from 1 to 4 carbons; and
n is an integer from 0 to 10;

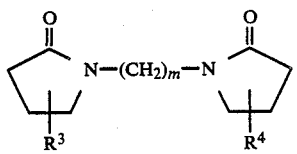

wherein
$R^3$ and $R^4$ are each hydrogen or a lower alkyl group having from 3 to 4 carbons; and
m is an integer from 1 to 18; or

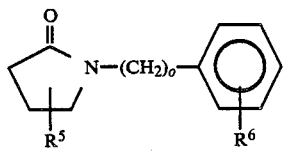

wherein
$R^5$ and $R^6$ are each hydrogen or lower alkyl having from 1 to 4 carbons; and
o is an integer from 0 to 10.

5. The method of claim 4 wherein the penetration enhancing agent is a compound of Formula I.

6. The method of claim 5 wherein the penetration enhancing agent is 1-dodecylazacycloheptan-2-one.

7. A method for treating psoriasis consisting essentially of applying a therapeutically sufficient quantity of a composition consisting essentially of 5-fluorouracil dissolved in a penetration enhancing agent to a psoriatic lesion until remission occurs, the composition being applied in one or more pulses at from 3 to 30 day intervals, each pulse comprising applying the composition to the lesion one or more times over a period of up to 48 hours.

8. The method of claim 7 wherein the penetration enhancing agent includes propylene glycol.

9. The method of claim 8 wherein a solution of from 0.001 to 5 wt. % 5-fluorouracil in propylene glycol is applied to the psoriatic lesion.

10. The method of claim 7 wherein the penetration enhancing agent includes a compound of Formula I, II or III:

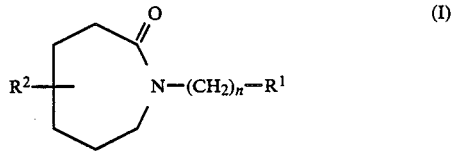

wherein
$R^1$ is a straight or branch chain alkyl group having from 1 to 18 carbons or aryl group having from 6 to 10 carbons;
$R^2$ is hydrogen or lower alkyl having from 1 to 4 carbons; and
n is an integer from 0 to 10;

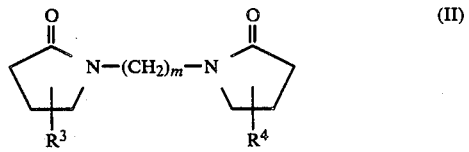

wherein
$R^3$ and $R^4$ are each hydrogen or a lower alkyl group having from 3 to 4 carbons; and
m is an integer from 1 to 18; or

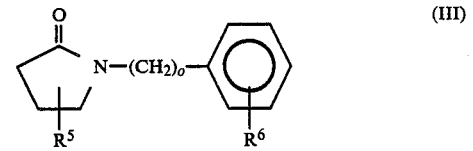

wherein
$R^5$ and $R^6$ are each hydrogen or lower alkyl having from 1 to 4 carbons; and
o is an integer from 0 to 10.

* * * * *